US008580301B2

(12) United States Patent
Poestges et al.

(10) Patent No.: US 8,580,301 B2
(45) Date of Patent: Nov. 12, 2013

(54) PSYCHOSTIMULANT CONTAINING PHARMACEUTICAL COMPOSITION

(75) Inventors: Reiner Poestges, Froendenberg (DE); Bernd Schneider, Iserlohn (DE); Richard Ammer, Iserlohn (DE)

(73) Assignee: PEJO Iserlohn Heilmittel und Diaet GmbH & Co. KG, Iserlohn (DE)

( * ) Notice: Subject to any disclaimer, the term of this patent is extended or adjusted under 35 U.S.C. 154(b) by 1143 days.

(21) Appl. No.: 11/710,170

(22) Filed: Feb. 23, 2007

(65) Prior Publication Data

US 2008/0075769 A1 Mar. 27, 2008

Related U.S. Application Data

(63) Continuation of application No. PCT/EP2005/009106, filed on Aug. 23, 2005.

(30) Foreign Application Priority Data

Aug. 23, 2004 (EP) .................................. 04019984
Sep. 28, 2004 (EP) .................................. 04023039

(51) Int. Cl.
*A61K 9/22* (2006.01)
(52) U.S. Cl.
USPC ............ 424/468; 424/458; 424/459; 424/462
(58) Field of Classification Search
USPC .................. 424/458, 459, 462, 468
See application file for complete search history.

(56) References Cited

U.S. PATENT DOCUMENTS

| 5,837,284 | A | 11/1998 | Mehta et al. | |
| 6,419,960 | B1 * | 7/2002 | Krishnamurthy et al. | 424/490 |
| 6,420,473 | B1 * | 7/2002 | Chittamuru et al. | 524/447 |
| 6,793,936 | B2 * | 9/2004 | Devane et al. | 424/484 |
| 2003/0170181 | A1 | 9/2003 | Midha | |

FOREIGN PATENT DOCUMENTS

| EP | 0 274 734 | 7/1988 |
| WO | WO97/03672 | 2/1997 |
| WO | WO98/14168 | 4/1998 |
| WO | WO 99/03471 A | 1/1999 |
| WO | WO99/16439 | 4/1999 |
| WO | WO 00/35450 A | 6/2000 |
| WO | WO 00/59479 A | 10/2000 |
| WO | WO2006/021426 | 3/2006 |

OTHER PUBLICATIONS

International Search Report corresponding to the PCT application No. PCT/EP05/09106 dated Mar. 28, 2006.
Notification of Transmittal of the International Preliminary Report on Patentability corresponding to the PCT application No. PCT/EP05/09106 dated Jun. 12, 2006.
Brown et al., "The Use of Methyphenidate for Cognitive Decline Associated with HIV Disease," Int'l. J. Psychiatry in Medicine. vol. 25, No. 1 pp. 21-37 (1995).
Conte et al., "A New Ibuprofen Pulsed Release Oral Dosage Form," Drug Development and Industrial Pharmacy. vol. 15, Nos. 14-16 pp. 2583-2596 (1989).
Firestone, "Factors Associated with Children's Adherence to Stimulant Medication," Amer. J. Orthopsychiat. vol. 52, No. 3 pp. 447-457 (1982).
Giunchedi et al., "Ketoprofen pulsatile absorption from 'multiple unit' hydrophilic matrices," International Journal of Pharmaceutics. vol. 77 pp. 177-181 (1991).
Holmes et al., "Psychostimulant Response in AIDS-Related Complex Patients," J. Clin. Psychiatry. vol. 50 pp. 5-8 (1989).
Shah et al., "Gel-Matrix Systems Exhibiting Bimodal Controlled Release for Oral Drug Delivery," Journal of Controlled Release. vol. 9 pp. 169-175 (1989).
Srinivas et al., "Enantioselective pharmacokinetics and pharmacodynamics of dl-threo-methylphenidate in children with attention deficit hyperactivity disorder," Clin. Pharmacol. Ther. vol. 52 pp. 561-568 (1992).

* cited by examiner

*Primary Examiner* — Sreeni Padmanabhan
*Assistant Examiner* — Shobha Kantamneni
(74) *Attorney, Agent, or Firm* — Jenkins, Wilson, Taylor & Hunt, P.A.

(57) ABSTRACT

The present invention is directed to a psychostimulant containing pharmaceutical composition comprising an enteric coating and showing a sustained release of said psychostimulant in vivo. The invention is further directed to the use of said pharmaceutical composition in the treatment of the Attention Deficit Hyperactivity Disorder (ADHD) and comorbidities, narcolepsy, fatigue and/or cognitive decline associated with systemic diseases such as acquired immunodeficiency syndrome or oncological diseases. Additionally, the present invention provides a method for the manufacture of said pharmaceutical composition.

5 Claims, 8 Drawing Sheets

Figure 2: Influence of the pH of the medium on the active substance dissolution from the enteric coated pellets: batch PL 3683 - Dissolution at a constant pH
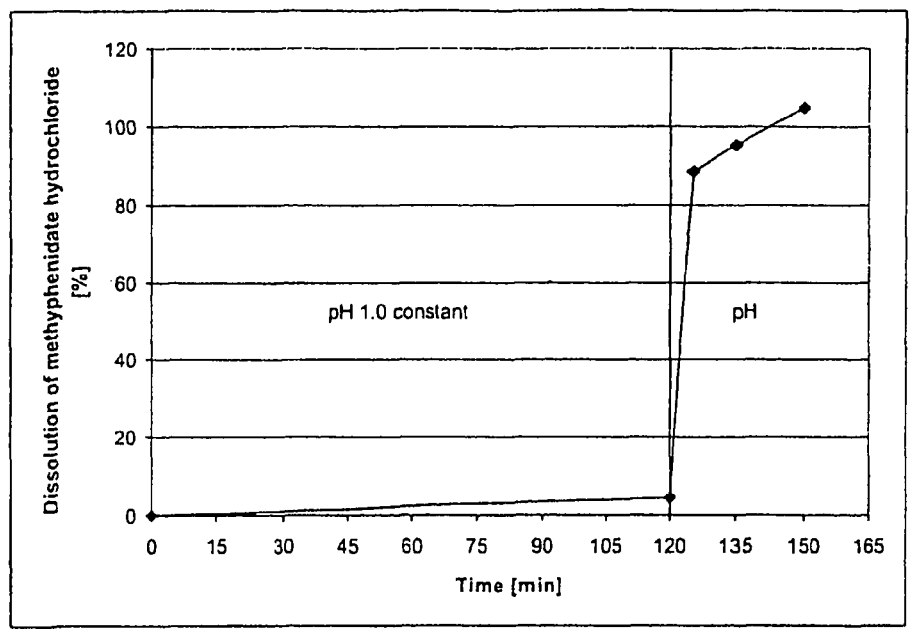
Figure 3: Influence of the pH of the medium on the active substance dissolution from the enteric coated pellets: batch PL 3683 - Dissolution at a rising pH
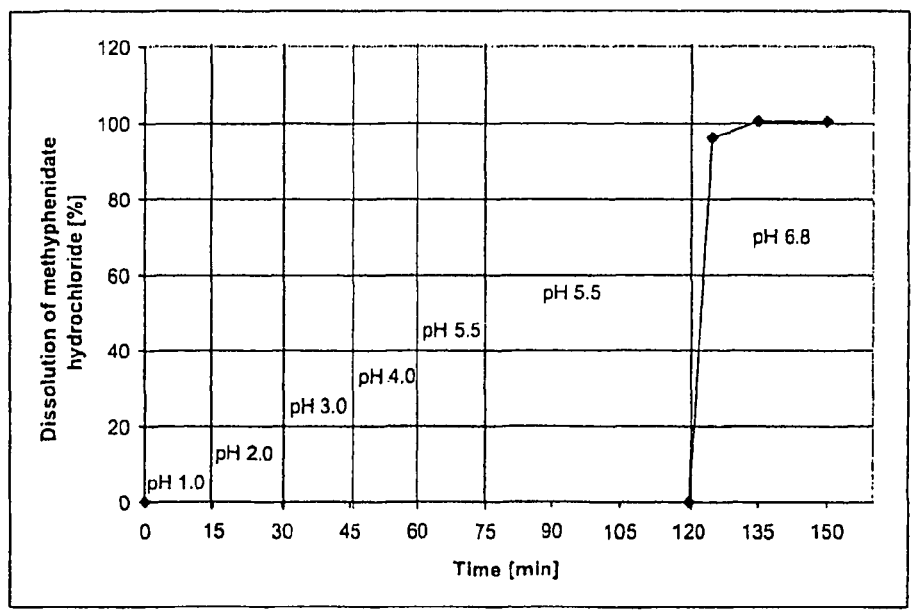

Figure 4: Active substance dissolution profiles for the *retard 10 mg Capsules*: batches PL 3691, PL 3692 and PL 3693 (each n = 6)
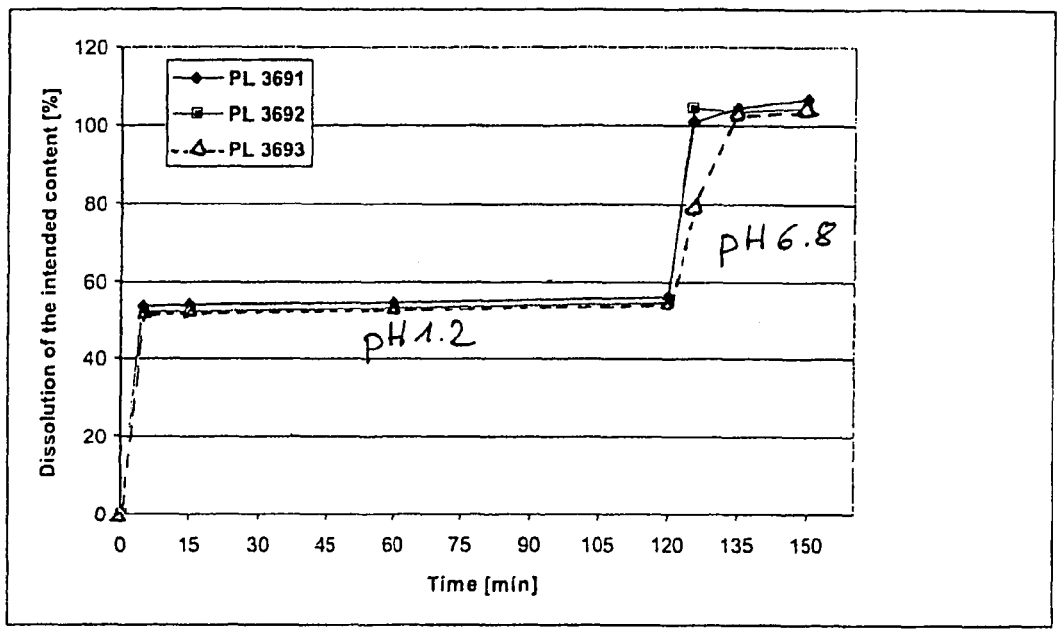
Summary: The results for the dissolution profiles of 3 batches demonstrate batch to batch conformity. The choice of the dissolution test is sufficient for the assessment of the dosage form.
A test for the disintegration time of the capsule will not be conducted.

Figure 5: Influence of the pH of the medium on the active substance dissolution from the capsules: batch PL 3691 - Dissolution of the declared amount at a constant pH
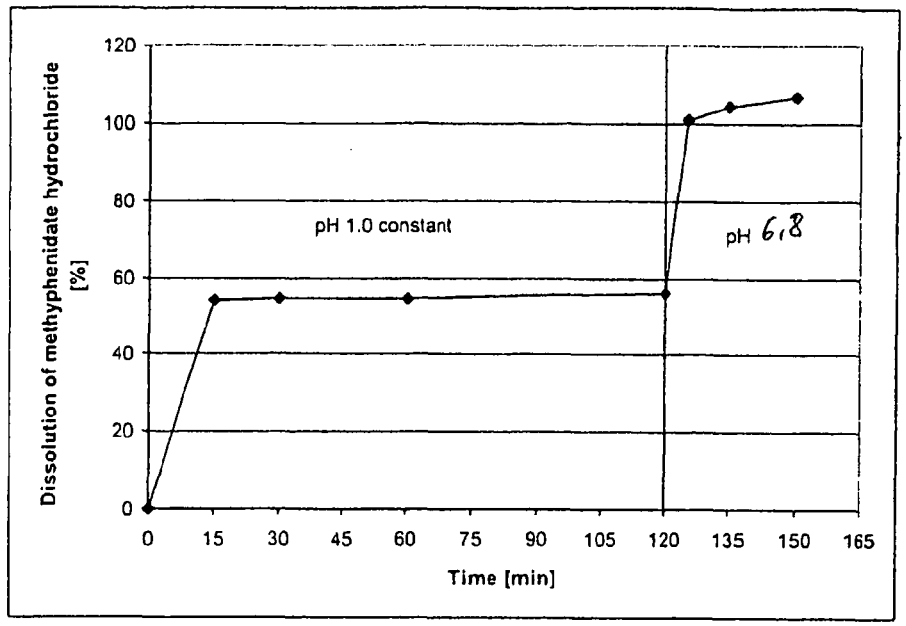
Figure 6: Influence of the pH of the medium on the active substance dissolution from the capsules: batch PL 3691-Dissolution of the declared amount at a rising pH
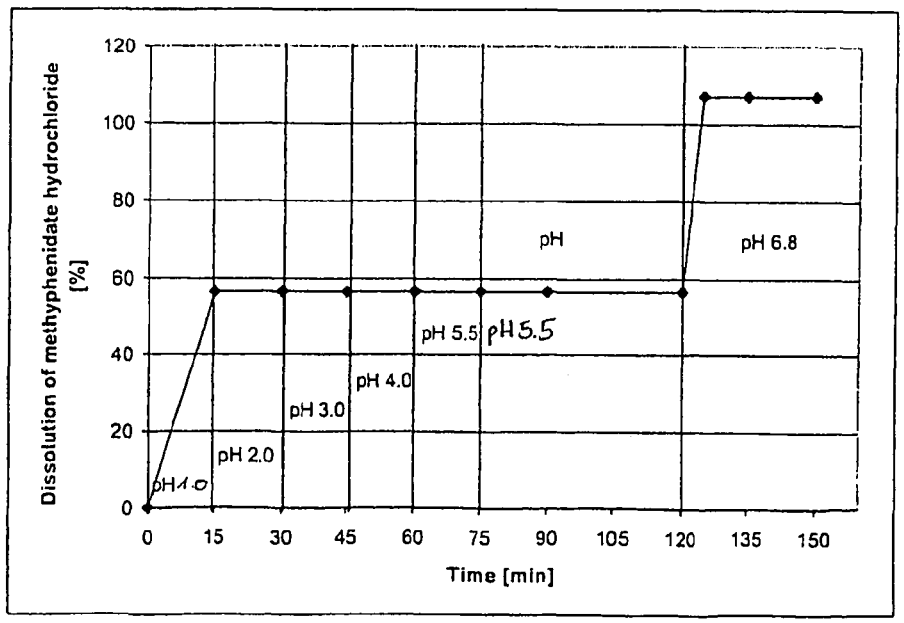

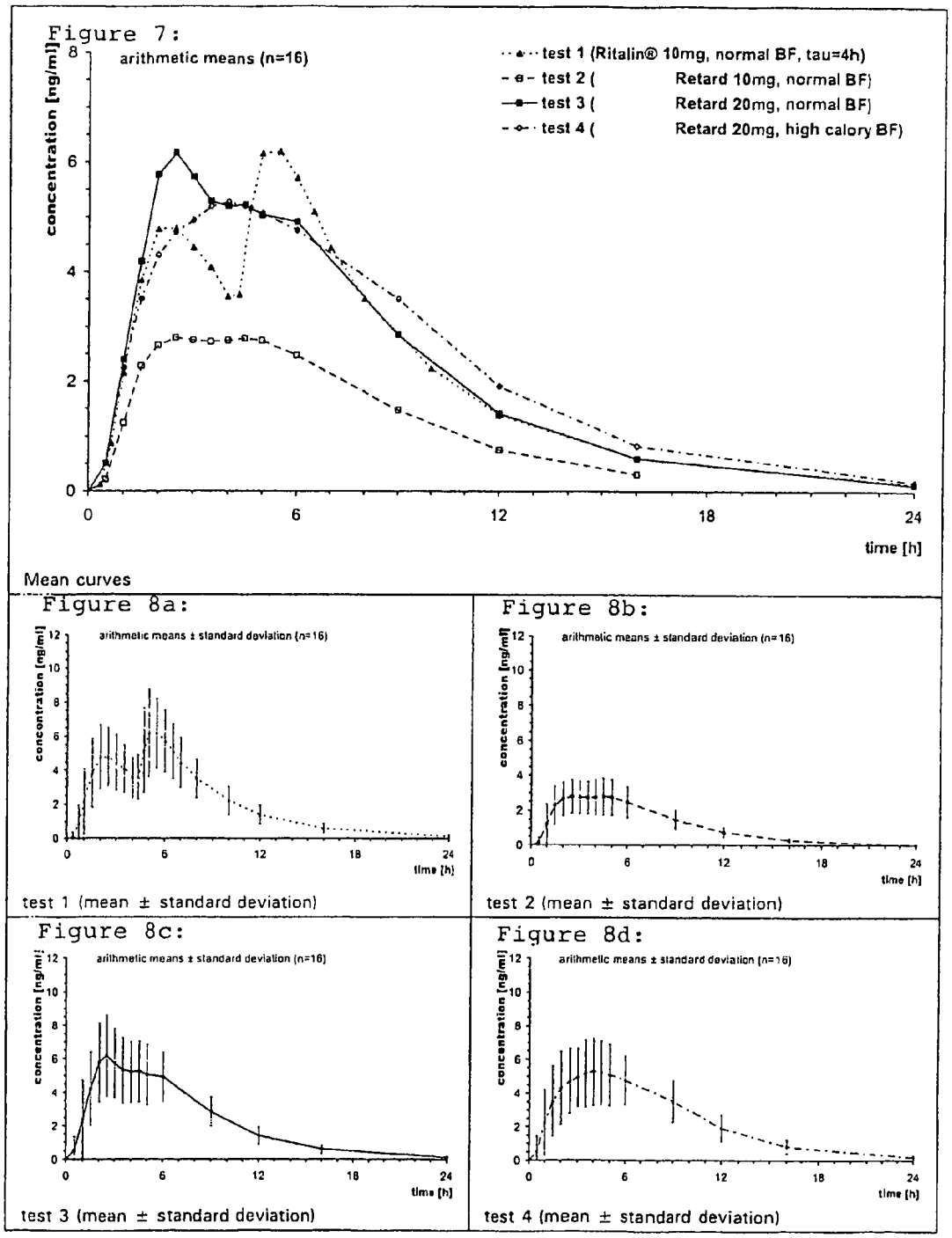

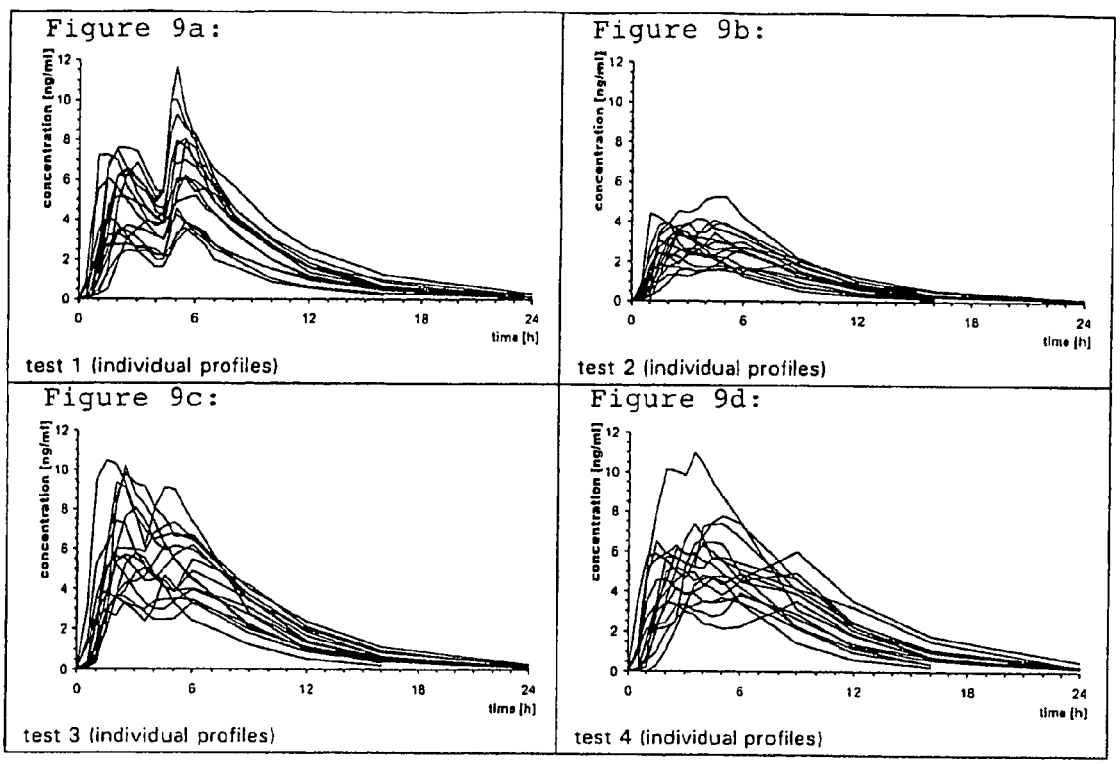

Figure 10: Dissolution profile batch PL 3691
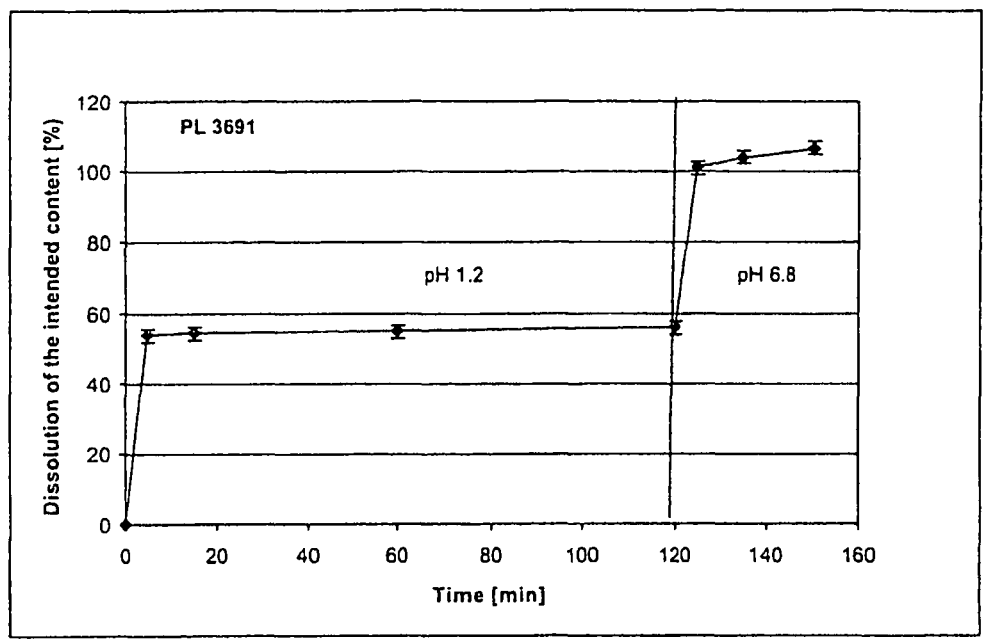

PSYCHOSTIMULANT CONTAINING PHARMACEUTICAL COMPOSITION

RELATED APPLICATIONS

This application is a continuation of PCT International Patent Application No. PCT/EP2005/009106, filed Aug. 23, 2005, which claims priority to European Patent Application No. 04019984.6, filed Aug. 23, 2004 and European Patent Application No. 04023039.3, filed Sep. 28, 2004, the disclosures of each of which are incorporated herein by reference in their entirety.

The present invention is directed to a psychostimulant containing pharmaceutical composition comprising an enteric coating and showing a sustained release of said psychostimulant in vivo. The invention is further directed to the use of said pharmaceutical composition in the treatment of the Attention Deficit Hyperactivity Disorder (ADHD) and comorbidities, narcolepsy, fatigue and/or cognitive decline associated with systemic diseases such as acquired immunodeficiency syndrome or oncological diseases. Additionally, the present invention provides a method for the manufacture of said pharmaceutical composition.

Attention Deficit Disorder (ADD), a commonly diagnosed nervous system illness in children, is generally treated with methylphenidate hydrochloride (available commercially as, e.g., Ritalin®). Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., Anti. J. Psych. Med. 25(1): 21-37 (1995); Holmes et al., J: Clin. Psychiatry 50: 5-8 (1989).

Methylphenidate is a racemate and is existing in four separate optical isomers, namely l-threo, d-threo, d-erythro and l-erythro. Pharmaceutically acceptable salts thereof are generally administered clinically.

Clinically, the threo pair of enantiomers of methylphenidate hydrochloride is generally administered for the treatment of ADD and ADHD. The hydrochloride salt is commonly referred to simply as "methylphenidate". Therefore, unless indicated otherwise, the term "methylphenidate" is used broadly herein to include methylphenidate and pharmaceutically acceptable salts thereof including methylphenidate hydrochloride.

The threo racemate (pair of enantiomers) of methylphenidate is a mild central nervous system stimulant with pharmacological activity qualitatively similar to that of amphetamines. Undesirable side effects associated with the use of the dl-threo racemate of methylphenidate include anorexia, weight loss, insomnia, dizziness and dysphoria.

Additionally, the racemate produces an euphoric effect when administered intravenously or through inhalation or ingestion, and thus carries a high potential for abuse.

Srinivas et al. studied the administration of dl-threo-, d-threo, and l-threomethylphenidate to children suffering from ADHD, and reported that the pharmacodynamic activity of dl-threo-methylphenidate resides in the d-threo isomer (Clin. Pharmacol. Ther., 52: 561-568 (1992)). Therefore, while dl-threo-methylphenidate is generally used therapeutically, this racemate includes the l-isomer which apparently makes no significant contribution to the pharmacological effectiveness of the drug, but likely contributes to the associated side effects. It is thus desirable to administer only the active d-threo form of the drug.

Immediate release methylphenidate preparations, because of their short half-life, require frequent administration at short intervals to ensure adequate treatment throughout a child's school day. The rapid onset and offset of immediate release methylphenidate (MPH) preparations means that a medicated child with attention deficit disorder will be maximally affected only for relatively brief periods during the day. Due to its short half-life, MPH is usually given twice per day, usually once after breakfast and once during the school day, an event that some children and some school personnel apparently avoid, resulting in poor compliance with prescribed regimens (Brown et al., 1985; Firestone 1982). Additionally, this creates a problem for school administrators who must store a controlled substance on school premises, with the associated risk that it may be stolen for improper use. Furthermore, children may be traumatized by ridicule from peers when they must take medication at school.

In the prior art, many approaches are existing to circumvent/overcome these problems.

It is known in the pharmaceutical art to prepare compositions which provide for sustained release of pharmacologically active substances contained in the compositions after oral administration to humans and animals. Sustained release formulations known in the art include specially coated pellets, coated tablets and capsules, and ion exchange resins, wherein the slow release of the active medicament is brought about through selective breakdown of the coating of the preparation or through compounding with a special matrix to affect the release of a drug. Some sustained release formulations provide a related sequential release of a single initial dose of an active compound and a subsequent dose at predetermined periods after administration.

For example, sustained release formulations of methylphenidate have been developed, which provide for slow release of the drug over the course of the day. A further approach resides in the provision of pulsed-release dosage forms, which mimic the effect of prior art medicaments administered on two or more time points during a day. The wash out period provided by the fall off of the plasma concentration of the active ingredient between peaks has been thought to be a contributing factor in reducing or preventing patient tolerance to various types of drugs. Therefrom, it was concluded that some of the therapeutic and pharmacological effects intrinsic in a pulsatile system may be lost or diminished as a result of the constant or nearly constant plasma levels achieved by, e.g., a zero-order release drug delivery systems.

Thus, a modified release composition or formulation which substantially mimics the release of frequent IR dosage regimes, while reducing the need for frequent dosing, was said to be desirable.

WO 98/14168 teaches a dosage form and a method of administering methylphenidate in a sustained and constantly ascending rate. The dosage form disclosed comprises a plurality of beads comprising a hydrogel matrix with increasing amounts of the active ingredient therein, coated with varying amounts of a release rate controlling material. Appropriate combinations of the active ingredient dose and the number and thickness coating layers can be selected to give an ascending release profile in which the plasma concentration of the active ingredient continually increases over a given period of time. However, WO 98/14168 is not teaching to achieve a rapid and high main peak plasma concentration, which is desirable in the treatment of, e.g. ADHD.

WO 97/03672 discloses that methylphenidate exhibits a therapeutic effect when administered in the form of a racemic mixture or in the form of a single isomer (such as the RR d-threo enantiomer).

WO 99/16439 teaches the chronic bolus administration of D-threo methylphenidate. The administration of the D-threo isomer eliminates adverse side effects associated with the DL racemate, and provides improved effectiveness. The compositions and methods of the invention are useful in treating nervous system disorders including attention deficit disorder, attention deficit hyperactivity disorder, and cognitive decline associated with systemic diseases such as acquired immunodeficiency syndrome.

Shah et al., J. Cont. Rel. (1989) 9: 169-175 disclose that certain types of hydroxypropyl methylcellulose ethers compressed into a solid dosage form with a therapeutic agent may give a bimodal release profile.

Giunchedi et al., Int. J. Pharm (1991) 77: 177-181 disclose the use of a hydrophilic matrix multiple-unit formulation for the pulsed release of ketoprofen. Giunchedi et al. teach that ketoprofen is rapidly eliminated from the blood after dosing (plasma half-life 1-3 hours) and consecutive pulses of drug may be more beneficial than constant release for some treatments. The multiple-unit formulation disclosed comprises four identical hydrophilic matrix tablets placed in a gelatin capsule.

Conte et al., Drug Dev. Ind. Pharm, (1989) 15: 2583-2596 and EP 0 274 734 (Phamidea Srl) teach the use of a three layer tablet for delivery of ibuprofen in consecutive pulses. The three layer tablet is made up of a first layer containing the active ingredient, a barrier layer (the second layer) of semi-permeable material which is interposed between the first layer and a third layer containing an additional amount of active ingredient. The barrier layer and the third layer are housed in an impermeable casing. The first layer dissolves upon contact with a dissolving fluid while the third layer is only available after dissolution or rupture of the barrier layer. In such a tablet the first portion of active ingredient must be released instantly. This approach also requires the provision of a semi-permeable layer between the first and third layers in order to control the relative rates of delivery of the two portions of active ingredient. Additionally, rupture of the semi-permeable layer leads to uncontrolled dumping of the second portion of the active ingredient which may not be desirable.

U.S. Pat. No. 5,837,284 discloses a methylphenidate dosage form having immediate release and delayed release particles. The delayed release is provided by the use of ammonio methacrylate pH independent polymers combined with certain fillers.

There remains a need for methods for delivering methylphenidate with maximum effectiveness and minimal potential for abuse.

Thus, it is an object underlying the present invention to provide a dosage form containing a psychostimulant which provides, in one administration, a rapid and high initial release of the drug followed by a second release, in order to provide optimum in vivo release and therefore treatment conditions of several diseases.

These objects are solved by the subject-matter of the independent claims. Preferred embodiments are set forth in the dependent claims.

It surprisingly turned out that a pharmaceutical composition containing an initial dosage of a psychostimulant and a second dosage of said psychostimulant, wherein the release of said second dosage is modified by an enteric coating comprising (co-)polymers of (meth)acrylic acid and/or (meth) acrylate containing carboxyl groups, is providing a sustained release of said second dosage of psychostimulant in vivo. This is surprising since an enteric coating as it is commonly used in the prior art should provide for a delayed release of the second dosage in vivo, which is contained in said enteric coated dosage form. I.e., it should be expected to cause two distinct peak plasma concentrations. However, the inventors found that not a delayed release, but, in contrast thereto, a sustained release appeared in vivo after administering the pharmaceutical composition of the present invention, showing essentially only one single main plasma concentration or a high first peak plasma concentration followed by a second lower peak plasma concentration (caused by the second dosage containing an enteric coating).

The usual behaviour of such an enteric coated drug, which could be expected based on the prior art knowledge is a rapid release of an initial dosage (acidic media) and a delayed, but also rapid release of a further dosage of the drug, as soon as the pH conditions allowed a removal (dissolution) of the enteric coating. Unexpectedly, the inventors recognized that the in vivo and in vitro behaviour of the pharmaceutical composition of the present invention differed substantially from the expected values: also in vivo, the initial dosage, which is immediately released, should cause a first peak plasma concentration followed by a second peak plasma concentration having the same or an even higher peak plasma concentration than the first peak plasma (based on identical amounts of the first and second dosages) as soon as the pharmaceutical composition reaches the intestine and releases the second dosage.

However, as it can be seen in FIG. 7-9, the plasma concentration after single administration of the pharmaceutical composition of the invention substantially follows a combined release pattern showing elements of a pulsatile release and of a sustained release regimen: it is released into the body steadily, over a long period of time (it is noted that in contrast thereto, a prolonged release dosage form is such that its activity continues for a longer time than conventional drugs, however, the retard effect is considerably shorter than in sustained release dosage forms).

Therefore, the present invention provides, according to a first aspect, a pharmaceutical composition containing an initial dosage of a psychostimulant and a second dosage of said psychostimulant, wherein the release of said second dosage is modified, characterized in that the release of said second dosage is modified by an enteric coating comprising (co-)polymers of (meth)acrylic acid and/or (meth)acrylate containing carboxyl groups, thereby causing a sustained release of said second dosage of the psychostimulant in vivo.

In addition to the above explanations, it can be said that the pharmaceutical composition of the present invention has a combined in vivo release pattern, i.e. a release pattern, which is characterised by two different release behaviours: the first being a pulsatile, the second being a sustained release of the psychostimulant in question. In this connection, it is referred to FIGS. 7-9 and 11 which clearly show that (under the assumption of two identical dosages for the first and second dosage) a first and highest peak is rapidly reached following release of the initial dosage of the psychostimulant and, thereafter, a lower second peak can be seen which is due to the second dosage the release of which is modified by an enteric coating.

This, however, is surprising and unexpected, since based on the usual knowledge and prior art compositions which are for example reflected in test 1 of FIG. 7 (Ritalin®, 10 mg) the skilled person would expect a lower first and a higher second peak in the in vivo release of the psychostimulant.

The inventors do not want to be bound to a specific theory, however, it is expected that the addition of an alkaline agent in the method of producing the pharmaceutical composition of the present invention is leading to a partial neutralisation of the carboxyl groups of the polymer forming the enteric coating and thus is leading to the formation of small channels in the enteric coating which allow a slight diffusion of the psychostimulant through that coating even at a pH of below 5.5 which typically is present in the stomach of human patients.

It is noted that the first in vitro experiments performed by the inventors did not point to the surprising in vivo results. As it can be seen in the figures, in particular in FIGS. 3 and 6, the above effect could not be determined by the original test method used for the in vitro release of a) the enteric coated pellets (FIG. 3) and b) the complete composition (FIG. 6). The enteric coating proved to be tight and acid resistant under these circumstances. However, the in vivo results clearly differed from that and showed the above explained sustained release effect of the enteric coating. Further investigations performed by the inventors showed that the specific test system used in FIGS. 3 and 6 was responsible for these inconsistent original results. This test system involved the introduction of the pellets/compositions in a solution of pH 1 at first and then immersing the same in solutions of pH 2, 3 etc. and the effect could not be shown. In later tests (see FIG. 11) however, the composition was directly introduced into a solution having pH 2 and only in this setting, which resembles the in vivo conditions much more than the original test, the above effect could be shown.

Therefore, the present pharmaceutical composition provides a modified in vivo release of the psychostimulant, in particular methylphenidate, and is leading to the following release pattern: the first and highest blood plasma concentration can be reached soon after intake of the pharmaceutical composition, i.e. within a short term following breakfast. Therapeutically, a high first concentration of the psychostimulant, for example methylphenidate, in the morning is wanted.

A second, slightly lower peak is generated in a time range of about 6 hours following intake of the pharmaceutical composition, corresponding to the time point of about noon. Especially in the therapy of ADHD it is therapeutically wanted that the noon dosage of the pharmaceutical composition being slightly lower than the morning dosage. Therefore, the present invention perfectly fulfills the requirement to have an optimum treatment of ADHD with only one intake of a pharmaceutical composition per day.

Taking Eudragit L 30 D-55 as a specific example of an enteric coating, the skilled artisan will expect a "tight" film to be formed (tight under acidic conditions) since it is known that methacrylic acid-ethylacrylate copolymer (1:1) dissolves only at a pH value of above pH 5.5. Therefore, the skilled person would expect that at a pH value of about pH 2.0 no psychostimulant, for example methylphenidate-HCl, will be released. Therefore, it could be expected that, based on a pharmaceutical composition of the invention having identical dosages in the first and the second dosage (50 weight-% each) exactly 50% of the overall content of the psychostimulant should be released in the acidic medium and the remaining 50% should be released after raising the pH to a value of more than pH 5.5 (for example pH 6.8).

Based on the assumed in vitro release it should be further expected to have a biphasic, pulsatile drug release in vivo having two essentially identical main peaks (one for the first, one for the second dosage) or as explained above for Ritalin®, a first peak lower than the second peak. This, however, is not the case with the present pharmaceutical composition, see in particular FIGS. 7 and 8 of the present application.

In an experimental setting it surprisingly turned out that the above effects can be achieved in the pharmaceutical composition of the invention by adding an alkaline agent to the suspension containing the polymers for the enteric coating, for example Eudragit L 30 D-55, the alkaline agent for example being sodium hydroxide (NaOH) in a concentration of 1 N. In the experiments, an amount of 1 N sodium hydroxide in exactly 10 vol.-% of the provided Eudragit L30 D-55 was used.

Taking these amounts of alkaline agent and polymer into consideration, it can be expected that the carboxyl groups of the polymer are partially neutralised in an amount of about 6%. In this connection, it is referred to FIG. 11 which is showing the in vitro release of the pharmaceutical composition of the present invention. In a time period of 120 minutes, about 70% of the overall drug amount is released. This amount is due to the amount of drug contained in the initial dosage (50% of the overall dosage in this example) and a part of the further 50% of the overall dosage which is released by the second dosage (on which an enteric coating is coated). This effect can be achieved already at a pH of 2.0.

As mentioned above, this effect is presumably due to "diffusion channels" which are formed by the partial neutralisation of free carboxyl groups contained in the polymer.

The term "(co-)polymers of (meth)acrylic acid and/or (meth)acrylate" comprises all polymers and copolymers based on methacrylic acid and acrylic acid as well as their derivatives. For example, by "(meth)acrylate" monomers are meant derived from methacrylic acid and/or acrylic acid (i.e., methacrylic esters and acrylic esters, methacrylic hydroxyalkyl esters and acrylic hydroxyalkyl esters, etc.). Furthermore, the term also encompasses polyacrylate polymers. As mentioned above, those polymers are comprised by the present invention, which are containing carboxyl groups.

The term "initial dosage" as used herein is defined as a dosage intended for immediate release of the psychostimulant after administration. In other words, an initial dosage is such a dosage, which is not coated by any means, which could delay or sustain the release of the psychstimulant under physiological conditions, i.e. the conditions present in the gastrointestinal tract.

The second dosage of the psychostimulant is effectively hindered from being released during passage through the stomach and will be effectively released as soon as it reaches the intestine.

In a certain embodiment of the invention, the sustained release formulation is based on a multi-layered release technology, and the drug product can be in an oral capsule containing pellets. In the case of pellets, encapsulated in a capsule, each pellet contains a series of layers with different characteristics: an outer immediate release layer and an inner release delaying layer (enteric coat). The formulation in this case is designed such that upon oral administration, the formulation provides a rapid dissolution and absorption of the outer layer of the formulation which contains a portion of the psychostimulant in immediate release form, thereby resulting in a rapid rise of the psychostimulant to therapeutic plasma levels. This is followed by a period of no absorption (due to an enteric coating), followed thereafter by a sustained release of the psychostimulant from the formulation to maintain plasma levels.

However, in a preferred embodiment, the pharmaceutical composition comprises two distinct components, the first component containing the initial dosage, the second component containing the dosage showing a modified release. This approach facilitates the overall manufacture of the product and is leading to optimum plasma concentrations in vivo and is therefore particularly preferred.

It is noted in this connection that the distribution of psychostimulant between the initial dosage and the second dosage led to optimum plasma concentration, whenever the amounts of psychostimulant used in both dosages were substantially equal. Therefore, a distribution of the psychostimulant of from 41:59%, to 59 to 41% by weight between the dosages is in particular preferred. A distribution of about 50:50% by weight is most preferred.

In a further preferred embodiment, the pharmaceutical composition of the invention is defined as causing a sustained release of said second dosage of psychostimulant in vivo in the fed condition. "Fed" condition indicates that the test formulation is administered to the patients after they had eaten a normal or high calorie breakfast. The inventors found out that in this case, the sustained release of the overall composition of this invention was further optimized, leading to a rapid onset of release of psychostimulant and a long lasting therapeutic concentration thereof in the plasma in vivo.

According to a further preferred embodiment, the pharmaceutical composition of the invention (i.e. the second component thereof) comprises an enteric coating based on a methacrylic acid copolymer. As an example hereof, the well known products Eudragit® L 30 D and L 100, and preferably Eudragit® L 30 D, can be used for the manufacture of an enteric coating.

The EUDRAGIT®—grades for enteric coatings are based on anionic polymers of methacrylic acid and methacrylates. They contain —COOH as a functional group. They generally dissolve at ranges from pH 5.5 to pH 7. Examples hereof, which can be used in the present invention are as follows:

EUDRAGIT® L 30 D-55: pH dependent anionic aqueous polymer dispersion solubilizing above pH 5.5 for targeted drug delivery in the duodenum.

EUDRAGIT® L 100-55: Spray dried EUDRAGIT® L 30 D-55 which can be reconstituted for aqueous formulations for targeted drug delivery in the duodenum.

EUDRAGIT® L 100: pH dependent anionic polymer powder solubilizing above pH 6.0 for targeted drug delivery in the jejunum EUDRAGIT® S100: pH dependent anionic polymer powder solubilizing above pH 7.0 for targeted drug delivery in the ileum (information derived from the product description provided by the producer, Röhm GmbH & Co. KG, Darmstadt, Germany).

The psychostimulant used in the present composition is preferably selected from the group consisting of amphetamine, metamphetamine, amphetaminil, fenetylline, methylphenidate and prolintane or a pharmaceutically acceptable salt thereof, an enantiomer or mixtures thereof, or mixtures of said ingredients. However, it is noted that all other derivatives of amphetamine or all substances having an amphetamine like activity, can be incorporated in the pharmaceutical composition of the present invention.

In the pharmaceutical composition of the invention, the first and the second component preferably is present in spherical form, more preferably in pellet or sphere form. However, also other multiparticulate systems can be used, such as granules, spheroids, beads, ionexchange resin beads in order to obtain a desired sustained release of the psychostimulant. The pellets and all other pharmaceutical ingredients used in this invention are known and commonly used in the field of pharmaceutical technology and further information in this respect may be found, for example, in "Remington's Pharmaceutical Sciences", Mack Publishing Co., Easton, Pa., latest edition.

Preferably, the first component comprises spheres on which a liquid containing the psychostimulant is coated. The liquid is dried thereafter, leaving behind the dried psychostimulant on the sphere. Those spheres preferably are sugar spheres which act as carrier for the active substance. They are preferably consisting of a mixture of corn (maize) starch and sucrose.

The liquid preferably is a suspension and is containing one or more of the following ingredients:
Povidone K 30,
Talc, micronised,
Purified water,
2-Propanol, and
Methylphenidate.

Preferably, the active substance, e.g. methylphenidate hydrochloride, is applied onto the sugar spheres in the form of an aqueous-alcoholic suspension containing Povidone K 30 and talc. In the immediate release pellets Povidone K 30 acts as a binding agent for methylphenidate hydrochloride. Talc is used as a separating agent.

The spheres are preferably mixed with a mixture of micronised talc and colloidal anhydrous silica (preferably 50:50 w/w) subsequent to the step of coating the suspension on the spheres. This prevents the spheres from sticking to each other.

In the pharmaceutical composition of the invention, the first component may comprise the following manufacturing formula in parts per weight:
Methylphenidate hydrochloride 0.1800-0.3000
Sugar spheres 3.5000-5.0000
Povidone K 30 0.0100-0.0300
Talc, micronised 0.0400-0.0500
Purified water 1.0000-2.0000
2-Propanol 0.1000-0.2000
Mixture of micronised talc and colloidal anhydrous silica 0.0010-0.0040

Alternatively, the first component is comprising the following manufacturing formula in parts per weight:
Methylphenidate hydrochloride 0.4000-0.6000
Sugar spheres 1.5000-5.0000
Povidone K 30 0.0300-0.0500
Talc, micronised 0.0800-0.1000
Purified water 2.5000-2.8000
2-Propanol 0.2000-0.3000
Mixture of micronised talc and colloidal anhydrous silica 0.0020-0.0030

According to a preferred embodiment, for the manufacturing of the second component, the enteric coating is coated on the first component as defined hereinabove, contained in a suspension comprising one or more of the following ingredients:
Eudragit L 30 D-55,
Sodium hydroxide,
Talc, micronised,
Triethyl citrate,
Simeticone emulsion,
Purified water, and optionally a colorant.

Methacrylic acid—ethyl acrylate copolymer (1:1) is an enteric coating, which dissolves at a pH exceeding 5.5. Sodium hydroxide solution (15%) is used in the enteric coated pellets to stabilise the suspension (avoids the coagulation of solid substances). Triethyl citrate acts as softening agent. For reasons of drug safety the coated pellets may be dyed using, e.g., indigotine (E 132) and aluminium hydroxide in order to distinguish from the immediate release pellets. Simeticone (30%) emulsion is added to the suspension as an anti-foaming agent.

Both types of pellets may be coated with a mixture of talc and colloidal anhydrous silica in a ratio of 1:1 to prevent the pellets sticking to each other.

Preferably, the second component is comprising the following manufacturing formula in parts per weight:
Methylphenidate hydrochloride 0.1500-0.3000
Sugar spheres 2.5000-4.0000
Povidone K 30 0.0150-0.3000
Talc, micronised 0.0300-0.0500
Purified water 1.0000-2.0000
2-Propanol 0.1000-0.2000
Eudragit L 30 D-55 3.0000-4.0000
Sodium hydroxide 15% 0.1000-0.1500
Talc, micronised 0.5000-0.6000
Triethyl citrate 0.1000-0.2000
Indigotine lacquer (E 132) 0.0060-0.0100
Simeticone emulsion 0.0100-0.0200
Purified water 2.0000-3.0000
Mixture of micronised talc and colloidal anhydrous silica (50:50) 0.0020-0.0030

Alternatively, the second component is comprising the following manufacturing formula in parts per weight:
Methylphenidate hydrochloride 0.4000-0.6000
Sugar spheres 2.5000-5.0000
Povidone K 30 0.0400-0.0500
Talc, micronised 0.0900-0.1000
Purified water 2.0000-3.0000
2-Propanol 0.2000-0.3000
Eudragit L 30 D-55 3.0000-4.0000
Sodium hydroxide 15% 0.1000-0.1500
Talc, micronised 0.5000-0.6000
Triethyl citrate 0.1000-0.2000
Indigotine lacquer (E 132) 0.0060-0.0100
Simeticone emulsion 0.0100-0.0200
Purified water 2.0000-3.0000
Mixture of micronised talc and colloidal anhydrous silica 0.0020-0.0040

In this connection, it is noted that other well-known ingredients may be used in the composition of the present invention (and may replace others) as long as they fulfill the same requirements. For example, other binders might be used in place of Povidon K30.

In the pharmaceutical composition of the invention, the first and second components are preferably incorporated in a capsule, preferably a hard gelatine capsule, or in a sachet.

Whenever methylphenidate is used a psychostimulant, the overall content thereof per capsule is 5-60 mg, preferably 10, 20, 30, 40 or 60 mg. In case, the psychostimulant is methylphenidate or a pharmaceutically acceptable salt thereof, an enantiomer or mixtures thereof, the mean in vitro dissolution profile in aqueous media of pH 1-3, preferably 1.2, is such that 80-100% of methylphenidate contained in the first component are released within 30, preferably 20, more preferably 15 min. following administration, and 80-100% of methylphenidate contained in the second component are released within 30, preferably 20, more preferably 15 min. following administration in a second media having a pH of 6.5-7.2, preferably 6.8. It is noted that percentages in the in vitro dissolution profile (see Examples and Figures) are referring to the overall content of the pharmaceutical composition, not to the percentage of dissolution of the first and second component separately.

As mentioned above, the in vivo release of the pharmaceutical composition of the invention essentially is a sustained release, wherein the main peak plasma concentration of methylphenidate is reached between 0.5 and 5, preferably between 1 and 4, most preferably at about 2.5 hours following administration of said pharmaceutical composition. Preferably, the plasma concentration at about 8 h following administration of the pharmaceutical composition is between 30-80% of the main peak plasma concentration of methylphenidate.

Preferably, the in vivo release of methylphenidate from the pharmaceutical composition essentially is a sustained release, and there is a highest peak plasma concentration between 1 and 4 h after administration of the pharmaceutical composition.

According to second aspect, the present invention is directed to the use of a pharmaceutical composition as defined herein for the manufacture of a medicament in the treatment of Attention Deficit Hyperactivity Disorder (ADHD) and comorbidities (as for example Tic syndrome), narcolepsy, fatigue and/or cognitive decline associated with systemic diseases such as acquired immunodeficiency syndrome or oncological diseases. Or, in other words, the present invention also encompasses a method for the treatment of the human body, comprising the steps of administering an effective amount of the above defined pharmaceutical composition to a patient in need of such treatment.

According to a third aspect, a method for the manufacture of a pharmaceutical composition as defined herein is provided, comprising the steps of:
a) manufacturing the first component by:
   providing spheres,
   preparing a liquid containing a psychostimulant,
   coating the spheres with said liquid, and
   drying the coated spheres;
b) manufacturing the second component by:
   providing spheres manufactured in accordance with step a),
   preparing a liquid suitable for providing an enteric coating on said spheres, the liquid containing (co-)polymers of (meth)acrylic acid and/or (meth)acrylate having carboxyl groups and an alkaline agent,
   coating the spheres with said liquid, and
   drying the coated spheres.

According to a preferred embodiment, steps a) and/or b) further comprise the step of mixing the spheres with a mixture of micronised talc and colloidal anhydrous silica and/or sieving the spheres obtained.

The manufacturing formulas/ingredients defined hereinabove may preferably used in steps a) and/or b). The method of manufacture of the present invention may further comprise the step to incorporate components a) and b) in a hard gelatine capsule or sachet.

The method of manufacture of the present invention most preferably is performed in accordance with the FIG. 1 representing a flow chart of the manufacturing process of the pharmaceutical composition of the present invention. In particular by this specific method, the advantages and improved characteristics of the pharmaceutical composition of the invention can be achieved.

The method of the present invention preferably employs an alkaline agent selected from NaOH and KOH. However, every other alkaline agent may be used as long as it fulfills the requirement of providing at least a partial neutralisation of the COOH groups contained in the polymer of the enteric coating.

Preferably, the alkaline agent is added to the liquid in an amount sufficient to achieve a neutralisation of 2-10, preferably 3-8, most preferably about 6% of said carboxyl groups.

The first and the second component of the pharmaceutical composition preferably contain identical amounts of said psychostimulant, preferably of methylphenidate.

According to a further aspect, the present invention provides a pharmaceutical composition obtainable by the above method. The pharmaceutical composition obtainable by this method is showing an in vivo release having first ($C_{max1}$) and second peak ($C_{max2}$) plasma concentrations, wherein $C_{max1} > C_{max2}$. This condition is achieved by using identical amounts of psychostimulant in a pharmaceutical composition of the present invention.

Unless otherwise defined, all technical and scientific terms used herein have the same meaning as commonly understood by one of ordinary skill in the art to which this invention pertains. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention is now further illustrated by the accompanying drawings, in which:

FIG. 2 is showing the influence of the pH of the medium on the active substance dissolution from the enteric coated pellets of the invention;

FIG. 3 is showing the influence of the pH of the medium on the active substance dissolution from the enteric coated pellets at rising pH;

FIG. 4 is depicting active substance dissolution profiles for the 10 mg retard capsules of the present invention;

FIG. 5 is showing the influence of the pH of the medium on the active substance dissolution from the capsules of the invention;

FIG. 6 is showing the influence of the pH of the medium on the active substance dissolution from the capsules of the invention at rising pH;

FIG. 7-9 are showing the plasma concentration following administration of a reference (Ritalin®; test 1) and the pharmaceutical compositions of the invention (test 2-4);

FIG. 10 is showing the in vitro dissolution profile of a pharmaceutical composition of the present invention;

EXAMPLES

Method of Preparation

Manufacturing Formula
Methylphenidate Hydrochloride Pellets (Immediate Release)
Batch size: 4.31 kg pellets The manufacturing formula for the immediate release pellets is given in Table 1.

TABLE 1

Manufacturing formula of the immediate release pellets
Ingredients

Methylphenidate hydrochloride
Sugar spheres
Povidone K 30
Talc, micronised
Purified water*
2-Propanol*
Mixture of micronised talc and
colloidal anhydrous silica (50:50)

*Removed during drying operation

Methylphenidate Hydrochloride Pellets (Enteric Coated)
Batch size: 6.17 kg pellets The manufacturing formula is given in Table 2.

TABLE 2

Manufacturing formula for enteric coated pellets
Ingredients

Methylphenidate hydrochloride
Sugar spheres
Povidone K 30
Talc, micronised
Purified water*
2-Propanol*
Eudragit L 30 D-55**
Sodium hydroxide 15%**
Talc, micronised
Triethyl citrate
Indigotine lacquer (E 132)
Simeticone emulsion**
Purified water*
Mixture of micronised talc and
colloidal anhydrous silica (50:50)

*Removed during drying operation
**Water content not present in finished product Hard Gelatin Capsules

| | |
|---|---|
| Batch size: | 50,000 capsules size 3 |
| Size: | 3 |
| Colour of cap: | mauve |
| Colour of body: | white |

Manufacturing Process

The product is manufactured in accordance with Good Manufacturing Practice for pharmaceutical products (GMP).

Figure 1:
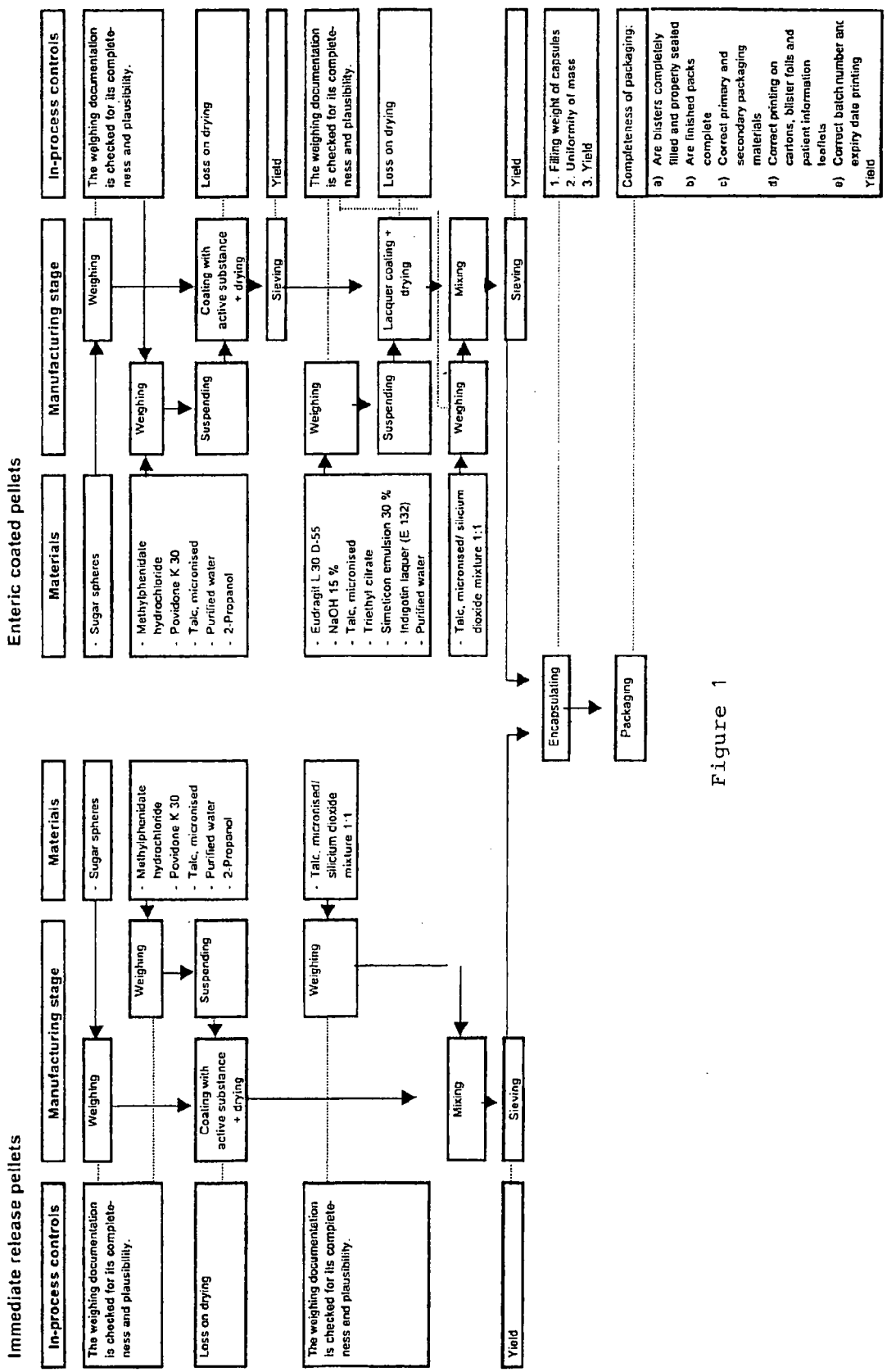
FIG. 1 is representing a flow chart of the manufacturing process of the pharmaceutical composition of the present invention.
Figure 11:
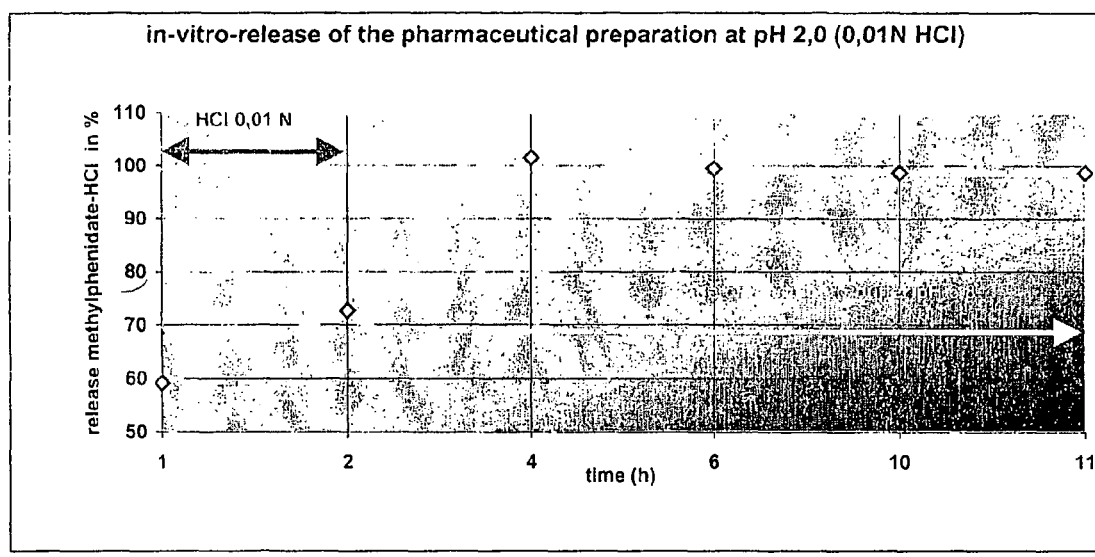
FIG. 11 depicts the in vitro release of a pharmaceutical composition of the present invention at pH 2.0.

A flow chart of the manufactory process is depicted in FIG. 1.

Process Description

Weighing of the Raw Materials

The weighing of the active substance and the excipients, required for a batch of retard 10 mg Capsules, is done using suitable scales.

Each raw material is weighed into a suitable, clearly labelled container.

Manufacture of the Pellets

Manufacture of the Immediate Release Pellets

Step 1: Preparation of the Active Substance Suspension

Povidone K 30 is dissolved in purified water by stirring for about 20 minutes. Methylphenidate hydrochloride and talc are dispersed into the solution for about 20-30 minutes using a disperser, finally 2-propanol is added over approximately 5 minutes. The final suspension is passed through a sieve, mesh 0.25 mm.

Step 2: Coating with Active Substance

The suspension is sprayed onto the sugar spheres using the fluid bed granulator. Afterwards the pellets are dried for about 5 minutes in a fluid bed granulator.

Step 3: Mixing

The pellets are mixed for about 15-20 minutes with a mixture of talc and colloidal anhydrous silica in the ratio 1:1.

Step 4: Sieving

The pellets are passed through a sieve, mesh 1.0 mm, all pellets larger than 1 mm are discarded.

Manufacture of the Enteric Coated Pellets

Step 1: Preparation of the Active Substance Suspension

Povidone K 30 is dissolved in purified water by stirring for approximately 20 minutes. Methylphenidate hydrochloride and talc are dispersed in the solution for 20-30 minutes using a disperser, finally 2-propanol is added over a period of approximately 5 minutes. The final suspension is passed through a sieve, mesh 0.25 mm.

Step 2: Coating with the Active Substance

The suspension is sprayed onto the sugar spheres using the fluid bed granulator. Afterwards the pellets are dried for about 5 minutes in a fluid bed granulator.

Step 3: Manufacture of the Lacquer Suspension

Solution 1: The 15% sodium hydroxide solution is added slowly and constantly with stirring into the Eudragit L 30 D-55 suspension.

Solution 2: Simeticone emulsion, talc, indigotin lacquer (E 132) and triethyl citrate are dispersed for 15-20 minutes in purified water, in a disperser.

Afterwards solution 2 is added to solution 1, with stirring.

The final suspension is passed through a sieve, mesh 0.25 mm.

Step 4: Coating of the Pellets

The suspension from step 3 is sprayed onto the pellets of step 2 using a fluid bed granulator. Afterwards the pellets are dried for approximately 10 minutes in a fluid bed granulator.

Step 5: Mixing

The pellets are mixed for 15-20 minutes with a mixture of talc and colloidal anhydrous silica in the ratio 1:1.

Step 6: Sieving

The coated pellets are passed through a sieve, mesh 1.0 mm, all pellets larger than 1 mm are discarded.

Encapsulation of the Immediate Release Pellets and the Enteric Coated Pellets

After determination of the methylphenidate content the weights for both pellet types are calculated according to the following equation:

$$\text{Capsule content in mg} = \frac{5 \text{ mg}}{\text{Content of MPD} - \text{HCl in mg}/1000 \text{ mg pellets}}$$

The amount of immediate release pellets and the enteric coated pellets calculated per capsule, is then filled into size 3 hard gelatin capsules using a capsule filling machine with two filling stations.

Packaging

The capsules are sealed into blister packs in the thermo-form-sealing station of the packaging line, at a sealing temperature of 210-220° C.

In the secondary packaging step, the blister packs along with patient information leaflet are placed into folding cartons at the boxing station of the packaging line.

Storage of Bulk Product

The intermediate products (immediate release pellets as well as enteric coated pellets) and the bulk product are stored for a maximum of 4 weeks, until further processing.

In-Process Controls

Weighing of the Raw Materials

The weighing documentation is checked for its completeness and plausibility.

Manufacture of the Immediate Release Pellets
Step 2: Coating with the Active Substance

| Loss on drying | |
| --- | --- |
| Specification: | <3.0% |
| Method: | Dried at 105° C. ± 5° C. for 2 hours (Ph. Eur. 2.2.32) |
| Sample size: | 1 g of substance |

Step 4: Sieving

| Yield | |
| --- | --- |
| Specification: | 97-100% < 1.0 mm |

Manufacture of the Enteric Coated Pellets
Step 2: Coating with the Active Substance

| Loss on drying | |
| --- | --- |
| Specification: | <3.0% |
| Method: | Dried at 105° C. ± 5° C. for 2 hours (Ph. Eur. 2.2.32) |
| Sample size: | 1 g of substance |

| Yield | |
| --- | --- |
| Specification: | 97-100% < 1.0 mm |

Step 4: Coating of the Pellets

| Loss on drying | |
| --- | --- |
| Specification: | <3.0% |
| Method: | Dried at 105° C. ± 5° C. until constant weight (Ph. Eur. 2.2.32) |
| Sample size: | 1 g of substance |

Step 6: Sieving

| Yield | |
| --- | --- |
| Specification: | ≥97% < 1.0 mm |

Encapsulation of the Immediate Release Pellets and the Enteric Coated Pellets

Samples are taken every 30 minutes at the beginning and during the capsulation process, the samples are then tested as follows:

| | |
| --- | --- |
| Filling weight of capsule: | ±10% |
| Sample size: | 20 capsules |
| | Uniformity of mass: |
| Specification: | Mean mass ± 10% |
| Method: | Ph. Eur. 2.9.5 |
| Sample size: | 20 capsules |
| | Yield |
| Specification: | at least 90-100% relative to the amount used. |

Packaging

Samples are taken every hour at the beginning and during the packaging process, the samples are then checked as follows:

a) Are blister strips completely filled and properly sealed
b) Are finished packs complete
c) Correct primary and secondary packaging materials used
d) Correct printing on the cartons, blister foils and patient information leaflets
e) Correct batch number and expiry date printing Yield Specification: at least 90-100% relative to the amount used.

Experimental Data for the Validation of the Manufacturing Process

The batch to batch reproducibility is confirmed by 3 certificates of analysis per strength and the comparative dissolution profiles. The medicinal product retard 10 mg Capsules consist of a hard gelatin capsule containing immediate release pellets and enteric coated pellets.

| Batch size: | |
|---|---|
| Immediate release pellets | 4.31 kg |
| Enteric coated pellets | 6.17 kg |

Manufacture of the Immediate Release Pellets

Critical Steps

The critical steps of the manufacturing of the immediate release pellets are the coating of the sugar spheres with the active substance methylphenidate hydrochloride and the following drying process. This takes place in a fluid bed granulator using the following process parameters:

| Coating | |
|---|---|
| Amount of inlet air: | 190-210 m³/h |
| Temperature of inlet air: | 48-52° C. |
| Spray rate: | 21.5 g/min |
| Spray pressure: | 0.9 bar |
| Drying | |
| Amount of inlet air: | 190-210 m³/h |
| Temperature of inlet air: | 48-52° C. |

Test

Active substance content
Loss on drying
Yield
Dissolution profile
Residual solvent test for 2-propanol Batches tested

PL 3653
PL 3658
PL 3661

TABLE 3

Active substance content/capsule content

| Batch | Specification | Methylphenidate hydrochloride/ g pellets | Resulting capsule content |
|---|---|---|---|
| PL 3653 | 52.0-61.0 mg | 53.1 mg | 94.2 mg |
| PL 3658 | methylphenidate | 54.0 mg | 92.6 mg |
| PL 3661 | hydrochloride/g pellets 82.0-96.2 mg pellets/capsule | 55.2 mg | 90.6 mg |
| Mean | | 54.1 mg | 92.5 mg |
| Relative standard deviation [%] | | 2.0 | — |

TABLE 4

Loss on drying

| Batch | Specification | Result |
|---|---|---|
| PL 3653 | ≤3% | 1.6% |
| PL 3658 | | 1.0% |
| PL 3661 | | 1.3% |
| Mean | | 1.3% |
| Relative standard deviation | | — |

TABLE 5

Yield

| Batch | Specification | Result |
|---|---|---|
| PL 3653 | >97% | 99.4% |
| PL 3658 | | 99.0% |
| PL 3661 | | 99.3% |
| Mean | | 99.2% |
| Relative standard deviation | | 0.2% |

TABLE 6

Data for the dissolution batch PL 3691

Dissolution [%] (with respect to the declared methylphenidate hydrochloride content of 10 mg/capsule)

| Release container | 1st stage in 0.1 N HCl pH 1.2 | | | | 2nd stage in buffer pH 6.8 | | |
|---|---|---|---|---|---|---|---|
| Basket (B) | 5 min | 15 min | 60 min | 120 min | 5 min | 15 min | 30 min |
| B 1 | 51.4 | 51.8 | 52.1 | 53.8 | 100.7 | 102.7 | 105.7 |
| B 2 | 51.6 | 52.3 | 52.7 | 53.6 | 100.2 | 103.1 | 105.0 |
| B 3 | 52.8 | 53.3 | 53.8 | 54.9 | 100.2 | 103.4 | 106.1 |
| B 4 | 56.3 | 57.1 | 57.7 | 59.1 | 102.1 | 106.2 | 109.2 |
| B 5 | 54.7 | 55.4 | 56.1 | 57.2 | 100.6 | 103.6 | 106.5 |
| B 6 | 54.7 | 55.2 | 55.6 | 56.7 | 101.7 | 104.7 | 107.3 |
| Specification | 40-60% | | 45-60% | | ≥80% | | |
| Mean | 53.6 | 54.2 | 54.7 | 55.9 | 100.9 | 04.0 | 106.7 |
| Relative standard deviation [%] | 3.7 | 3.8 | 3.9 | 3.9 | 0.8 | 1.2 | 1.4 |

See FIG. 10

Comparison of the Dissolution Profiles

The specification for the absolute dissolution rate of the capsules results from the separate specifications of the intermediate products:

A minimum of 80% after 15 minutes applies for the immediate release pellets. Hence, for this part of the immediate release pellets a minimum release of 4 mg is expected, this is equivalent to a 40% dissolution rate, with respect to the complete active substance part of the capsule.

TABLE 7

Table comparing the dissolution of the active substance

| Test | Specification | PL 3691 | PL 3692 | PL 3693 |
|---|---|---|---|---|
| Dissolution (n = 6) | With respect to 20 mg methylphenidate hydrochloride | | | |

TABLE 7-continued

Table comparing the dissolution of the active substance

| Test | Specification | PL 3691 | PL 3692 | PL 3693 |
|---|---|---|---|---|
| 1$^{st}$ stage at pH 1.2: | | | | |
| after 15 min | 40-60% | 54.2% | 52.3% | 51.4% |
| after 120 min | 45-60% | 55.9% | 54.3% | 52.9% |
| 2$^{nd}$ stage at pH 6.8: | | | | |
| after 15 min | ≧80% | 104.0% | 103.6% | 103.7% |

See FIG. 4

Dissolution of the Active Substance

Dissolution of the active substance is determined using an appropriate apparatus following the instructions in the European Pharmacopoeia (Ph. Eur. 2.9.3).

This method allows a quality assessment for the release of the methylphenidate hydrochloride content of each type of the pellets used.

Release of the active substance takes place in two stages. The aim is a dissolution profile, where in the 1$^{st}$ stage 5 mg methylphenidate hydrochloride from the immediate release pellets is dissolved in 0.1 N hydrochloric acid, and where in the 2$^{nd}$ stage 5 mg methylphenidate hydrochloride from the enteric coated pellets are dissolved immediately after change to a potassium dihydrogen phosphate buffer pH 6.8.

Ideally as little as possible of the active substance from the enteric coated pellets should be released in the hydrochloric acid during the 1$^{st}$ stage.

The pH is changed by exchanging the vessel underneath the basket with one containing the new pre heated medium for the 2$^{nd}$ stage. This exchange of the vessel is possible, because the size of the pellets inside the capsules is definitely larger than the meshes of the baskets.

The enteric coated pellets (perceptible through their light blue colour) remain within the baskets, hence the appropriate content of the active substance will not be released until the 2$^{nd}$ stage at pH 6.8.

Study to Evaluate the Discriminating Properties of the Method Used to Investigate the Release.

The influence of the sink conditions on the release profile is examined by monitoring the pH value of the medium during the 2$^{nd}$ stage. Because of the special properties of the excipient methacrylic acid ethyl acrylate copolymer (1:1) (Eudragit L 30 D-55) the pH-value is critical for the amount of active substance released and the delay of the release, respectively.

As a further parameter the stirrer speed was varied whereas the dissolution apparatus and the medium were kept the same.

Rationale for the Apparatus Used

The basket apparatus of Ph. Eur. 2.9.3 is used because otherwise the capsules would float on the surface. Also the basket apparatus is preferred to the paddle apparatus because it allows an exchange of the medium. The pellets used are larger than the mesh of the baskets.

Justification for the Medium Used

The aqueous media (0.1 N hydrochloric acid or 0.05 M potassium dihydrogen phosphate pH 6.8) as recommended by the FIP-guidelines for dissolution testing of solid oral products (Final Draft 1995), were used without any further additives, as methylphenidate hydrochloride is an extremely water soluble substance.

However, in an alkaline solution hydrolysis occurs.

The maximum daily dose of 60 mg methylphenidate hydrochloride dissolves easily in the buffer solutions of the European Pharmacopoeia, ie in 250 ml hydrochloric acid pH 1.2 as well as in 250 ml potassium dihydrogen phosphate buffer pH 4.6 or 6.8, respectively.

Influence of the pH Value of the Medium of the 1$^{st}$ Stage

The release from the medium during a constant pH of 1.0 over a 120 min period is compared with the release from the medium during a pH increase of 1.0 to 5.5.

Description of the Procedure

The release is tested exemplary on the intermediate product (enteric coated pellets), as well as the finished product (retard 10 mg Capsules).

A comparison with the immediate release pellets will not be conducted because, as already mentioned earlier, the active substance is easily soluble in all the European Pharmacopoeia buffers and it is expected that the pH-value has no relevance for the release behaviour.

The study on the dissolution from the intermediate product was conducted following the control tests as described for enteric coated pellets. The study on the dissolution from the capsules was conducted following the methods as described.

In each case the only modification to the control test was a change in the pH-value of the media. The 2' stage in 0.05 M potassium dihydrogen phosphate buffer, pH 6.8, was also conducted following the above control tests. The quantification of the released methylphenidate hydrochloride was carried out using HPLC.

The comparison is conducted on one example batch of the enteric coated pellets as well as on one batch of the finished product retard 10 mg Capsules, respectively.

Description of the pH changes: The pH is increased every 15 minutes by one unit, this is done for example, after the 15 minute sample has been taken, by moving the basket containing the pellets into) a new release-vessel containing 0.1 N hydrochloric acid, which has a pH of exactly 1.0. Successive samples are taken at 15 minute intervals during the stirring process. The manufacturer of Eudragit L 30 D-55 states that the formation of salt at the borderline pH-value of 5.5 is the reason for the disintegration of the Eudragit L 30 D-55 film. The value of 5.5 is kept over a time of 45 minutes (up to 120 minutes in total).

TABLE 8

Comparison of the values for release of the intermediate product, enteric coated pellets (batch PL 3683)

| Time in hydrochloric acid [min] | pH-value | Dissolution of the determined amount [%] | pH-value | Dissolution in % of the determined amount |
|---|---|---|---|---|
| 1$^{st}$ stage of dissolution in 0.1 N HCl, pH 1.0 | | | | |
| 0 | 1.0 | 0 | 1.0 | 0 |
| 15 | 1.0 | | 1.0 | n.d.* |
| 30 | 1.0 | | 2.0 | n.d.* |
| 45 | 1.0 | | 3.0 | n.d.* |
| 60 | 1.0 | | 4.0 | n.d.* |
| 75 | 1.0 | | 5.0 | n.d.* |
| 90 | 1.0 | | 5.5 | n.d.* |
| 120 | 1.0 | 4.4 | 5.5 | n.d.* |
| 2$^{nd}$ stage of dissolution in potassium dihydrogen phosphate buffer, pH 6.8 | | | | |
| 5 | 6.8 | 88.5 | 6.8 | 96.0 |
| 15 | 6.8 | 95.3 | 6.8 | 100.6 |
| 30 | 6.8 | 104.9 | 6.8 | 100.4 |

*n.d.: not detectable; limit of detection: 2.5%

See FIGS. 2 and 3

TABLE 9

Comparison of the values for release of the finished product, retard 10 mg Capsules (batch PL 3691)

| Time in hydrochloric acid [min] | pH-value | Dissolution of the determined amount [%] | pH-value | Dissolution in % of the determined amount |
|---|---|---|---|---|
| $1^{st}$ stage of dissolution in 0.1 N HCl, pH 1.0 | | | | |
| 0 | 1.0 | 0.0 | 1.0 | 0.0 |
| 15 | 1.0 | 54.2 | 1.0 | 56.3 |
| 30 | 1.0 | 54.3 | 2.0 | 56.3 |
| 45 | 1.0 | | 3.0 | 56.3 |
| 60 | 1.0 | 54.7 | 4.0 | 56.3 |
| 75 | 1.0 | | 5.0 | 56.3 |
| 90 | 1.0 | | 5.5 | 56.3 |
| 120 | 1.0 | 55.9 | 5.5 | 56.3 |
| $2^{nd}$ stage of dissolution in potassium dihydrogen phosphate buffer, pH 6.8 | | | | |
| 5 | 6.8 | 100.9 | 6.8 | 106.9 |
| 15 | 6.8 | 104.0 | 6.8 | 106.9 |
| 30 | 6.8 | 106.7 | 6.8 | 106.9 |

See FIGS. 5 and 6

The dissolution profile for the enteric coated pellets in diagram demonstrates that the protective properties of the Eudragit L 30 D-55 film are maintained constant up to a pH of 5.5. The sample profiles for the finished product retard 10 mg Capsules PL 3691 in diagram did not show any significant differences at a low or rising pH. Up to the limit of pH 5.5 the pellets retain their original shape in the baskets. This also demonstrates that the change in pH has no influence on the dissolution of the immediate release pellets. The required two-stage dissolution profile is reached at pH 1 to pH 5.5. The results are representative and transferable for all further batches of the intermediate and finished products.

Summary: an increase in the pH-value of the medium from pH 1 to pH 5.5 has not influence on the desired two-stage dissolution profile of the active substance.

Tolerance Limit for the pH of the 0.1 N Hydrochloric Acid Used for the Release Studies The tolerance limit for the pH of the 0.1 N hydrochloric acid, which is the test medium of the $1^{st}$ stage of dissolution, is between 0.8 and 1.2. This corresponds, after an exact titre determination, to a deviation from the norm of 0.06 N hydrochloric acid to 0.15 N hydrochloric acid. Hence, the 0.1 N hydrochloric acid can be manufactured without any further titre adjustment.

Variance in Stirrer Speed

In order to assess the effect of the stirrer speed, the release was compared exemplary for the intermediate products as well as for the finished product retard 10 mg Capsules.

The release from the intermediate products was investigated following the control tests in part II.D.3.1 for the immediate release pellets as well as the enteric coated pellets.

The release from the finished product was investigated following the control tests The only parameter to be changed in each case was the "stirrer-speed". This was reduced to 50 rotations per minute (rpm) in order to determine whether this increased the validity of the test.

Diagrams demonstrate the dissolution properties at a stirrer speed of 100 rpm compared to 50 rpm.

| | |
|---|---|
| Title of study: | Food Effect Study after Single Dose Oral Application of a 10 mg and a 20 mg Methylphenidate Hydrochloride Modified Release Preparation and b.i.d. Application of a 10 mg Methylphenidate Hydrochloride Immediate Release Preparation Following a Normal Breakfast and Single Dose Oral Application of the 20 mg Methylphenidate Hydrochloride Modified Release Preparation Following a High Calory Breakfast in 16 Healthy Volunteers |
| Protocol-No.: | |
| Date of the report: | |
| Investigators: | Principal investigator: |
| | Co-investigators: |
| Study centre: | |
| Time of clinical part: | Clinical Phase: I/IV |
| Objectives: | Aim of the present study was the investigation of the bioavailability of methylphenidate modified release 10 mg and 20 mg preparations after single dose application and a 10 mg methylphenidate immediate release preparation after b.i.d. application following a normal breakfast compared to single dose application of the 20 mg modified release preparation following a high calory breakfast. Bioavailability had to be compared to detect differences between the two fed conditions tested and between immediate release and modified release preparations. Determination of tolerability. |
| Study design: | single dose (except b.i.d. application of test 1) completely balanced randomized cross over open four way |
| Subjects (total and for each treatment): 16/16 | planned for completion: 16 (16 for each treatment) |
| | enrolled: 24 |
| | withdrawals: 1 (after pre-examination) |
| | not suitable: 4 |
| | reserve: 3 |
| | randomized: 16 |
| | completed as per protocol: 16 |
| Diagnosis and main criteria for inclusion: | male and female caucasians smoker/nonsmoker between 18 and 45 years of age healthy judged by means of laboratory tests and physical examination body weight within normal range signed written informed consent |

| | | |
|---|---|---|
| test 1 - preparation: | | Ritalin ®, tablet |
| | unit dose: | 10 mg methylphenidate hydrochloride |
| | mode/route: | oral |
| | regimen: | 2 × 1 tablet |
| | | 10 mg after normal breakfast, 10 mg 4 h later |
| | batch no: | S87900 |
| test 2 - preparation: | | Retard 10 mg, capsule |
| | unit dose: | 10 mg methylphenidate hydrochloride |
| | mode/route: | oral |
| | regimen: | 1 × 1 single dose of one capsule |
| | | after normal breakfast |
| | batch no: | PL 3780 |
| test 3 - preparation: | | Retard 20 mg, capsule |
| | unit dose: | 20 mg methylphenidate hydrochloride |
| | mode/route: | oral |
| | regimen: | 1 × 1 single dose of one capsule |
| | | after normal breakfast |
| | batch no: | PL 3781 |
| test 4 - preparation: | | Retard 20 mg, capsule |
| | unit dose: | 20 mg methylphenidate hydrochloride |
| | mode/route: | oral |
| | regimen: | 1 × 1 single dose of one capsule |
| | | after high calory breakfast |
| | batch no: | PL 3781 |
| Duration of treatment: | 24 hours/treatment period; wash-out phases: seven days each | |
| Blood sampling points: | test 1: | 0 (blank), 0.33, 0.67, 1, 1.5, 2, 2.5, 3, 3.5, 4, 4.33, 4.67, 5, 5.5, 6, 6.5, 7, 8, 10, 12, 16, and 24 hours |
| | | (22 samples/volunteer and treatment period; plasma) |
| | test 2-4: | 0 (blank), 0.5, 1, 1.5, 2, 2.5, 3, 3.5, 4, 4.5, 5, 6, 9, 12, 16, and 24 hours |
| | | (16 samples/volunteer and treatment period; plasma) |
| Analytical Method: | GC/MS | |
| | Quantification limit: | 0.072 ng methylphenidate/ml plasma |
| | Validation range: | linear within 0.072 ng and 18.25 ng MPH/ml plasma |
| | Inter-assay-variance: | 0.365 ng/ml    4.37 CV % |
| | | 3.65 ng/ml    2.44 CV % |
| | | 14.6 ng/ml    2.09 CV % |
| | Criteria for evaluation: | |
| | Pharmacokinetics: | |
| Primary parameter: | $AUC_{0-t_{last}}$ (extent of bioavailability) | |
| Secondary parameter: | $c_{max}$, $t_{max}$ (rate of bioavailability) | |
| Descriptive parameters: | $AUC_{0-\infty}$, $t_{1/2}$, $MRT_{0-t_{last}}$, HVD, $t_{75\% c_{max}}$ | |
| Safety: | Blood pressure, pulse rate, ECG, laboratory examinations and subject findings/adverse events, tolerability | |
| | Statistical methods: | |
| Pharmacokinetics: | parametric (ANOVA)/non-parametric (Wilcoxon-Mann-Whitney tests) | |
| | logarithmic transformation (ratios: AUC, $c_{max}$), untransformed analysis (differences: $t_{max}$) | |
| | 90% confidence intervals | |
| Safety: | Listing of individual data | |
| | Descriptive statistics | |

TABLE 10

Results:
Pharmacokinetics:

| | variable | geometric mean [1] | ±SD | arithmetic mean | ±SD | range |
|---|---|---|---|---|---|---|
| Test 1: | $AUC_{0-tlast}$ [ng · h · ml$^{-1}$] | 45.98 | 16.66 | 48.74 | 16.36 | 25.88-74.30 |
| | $c_{max}$ [ng/ml] | 6.20 | 2.24 | 6.60 | 2.44 | 3.64-11.65 |
| | $t_{max}$ [h] | 5.00 | — | 4.79 | 1.34 | 1.50-6.00 |
| Test 2: | $AUC_{0-tlast}$ [ng · h · ml$^{-1}$] | 24.43 | 8.33 | 25.73 | 8.14 | 12.80-41.34 |
| | $c_{max}$ [ng/ml] | 3.11 | 1.05 | 3.27 | 1.02 | 1.59-5.23 |
| | $t_{max}$ [h] | 4.50 | — | 3.88 | 1.57 | 1.00-6.00 |
| Test 3: | $AUC_{0-tlast}$ [ng · h · ml$^{-1}$] | 48.92 | 15.07 | 51.07 | 14.97 | 30.39-74.60 |
| | $c_{max}$ [ng/ml] | 6.42 | 2.21 | 6.78 | 2.26 | 3.49-10.46 |
| | $t_{max}$ [h] | 2.75 | — | 3.22 | 1.37 | 1.50-6.00 |

TABLE 10-continued

Results:
Pharmacokinetics:

| | variable | geometric mean [1] | ±SD | arithmetic mean | ±SD | range |
|---|---|---|---|---|---|---|
| Test 4: | $AUC_{0-tlast}$ [ng · h · ml$^{-1}$] | 51.78 | 14.99 | 53.80 | 14.96 | 33.90-79.75 |
| | $c_{max}$ [ng/ml] | 5.62 | 1.69 | 5.87 | 1.87 | 3.48-10.98 |
| | $t_{max}$ [h] | 4.25 | — | 4.44 | 2.24 | 1.50-9.00 |

[1] median is given for $t_{max}$ instead

TABLE 11

| bioavailability analyses | | point estimate | confidence limits | intra-individual CV(%) |
|---|---|---|---|---|
| Test 3: | $AUC_{0-tlast}$ [% of test 1] | 106.4 | 101.3-111.7 | 8.23 |
| | $c_{max}$ [% of test 1] | 102.1 | 95.0-109.6 | 12.0 |
| | $t_{max}$ [Δ to test 1] | −1.75 | −2.75-0.75 | |
| Test 2: | $AUC_{0-tlast}$ [% of test 3] | 49.9 | 47.6-52.4 | 8.23 |
| | | 99.9 [2] | 95.1 [2]-104.9 [2] | |
| | $c_{max}$ [% of test 3] | 48.4 | 45.1-52.0 | 12.0 |
| | | 96.8 [2] | 90.2 [2]-104.0 [2] | |
| | $t_{max}$ [Δ to test 3] | +0.50 | −0.25-+1.50 | |
| Test 4: | $AUC_{0-tlast}$ [% of test 3] | 105.8 | 100.8-111.1 | 8.23 |
| | $c_{max}$ [% of test 3] | 87.5 | 81.5-94.0 | 12.0 |
| | $t_{max}$ [Δ to test 3] | +1.13 | ±0.00-+2.00 | |

[2] normalized to a dose of 20 mg

See FIGS. 7-9

What is claimed is:

1. A method for the manufacture of a pharmaceutical composition comprising two distinct components, the first component containing an initial dosage of a psychostimulant and the second component containing a second dosage of said psychostimulant, wherein said psychostimulant is methylphenidate, and wherein the release of said second dosage is modified, characterized in that the release of said second dosage is modified by a single layer coating, wherein the single layer coating is an enteric coating comprising (co-)polymers of (meth)acrylic acid and/or (meth)acrylate containing carboxyl groups, thereby causing a sustained release of said second dosage of the psychostimulant in vivo, and wherein the in vivo release of the pharmaceutical composition is characterized by one single main plasma peak, comprising the steps of:

a) manufacturing the first component by:
   providing spheres,
   preparing a liquid containing a psychostimulant,
   coating the spheres with said liquid, and
   drying the coated spheres;
b) manufacturing the second component by:
   providing spheres manufactured in accordance with step a),
   preparing a liquid suitable for providing an enteric coating on said spheres, the liquid containing (co-)polymers of (meth)acrylic acid and/or (meth)acrylate having carboxyl groups and an alkaline agent selected from the group consisting of NaOH and KOH, wherein the alkaline agent is added to the liquid in an amount sufficient to achieve a neutralization of 3-8% of said carboxyl groups,
   coating the spheres with said liquid, and
   drying the coated spheres, thereby forming an enteric coating layer comprising channels which allow for diffusion of the psychostimulant through the enteric coating layer at a pH below 5.5.

2. The method of claim 1, wherein steps a) and/or b) further comprise the step of mixing the spheres with a mixture of micronised talc and colloidal anhydrous silica and/or sieving the spheres obtained.

3. The method of claim 1, wherein components a) and b) are incorporated in a hard gelatine capsule or sachet.

4. The method of claim 1, wherein the first and the second component of the pharmaceutical composition contain identical amounts of said psychostimulant.

5. The method of claim 1, wherein the alkaline agent is added to the liquid in an amount sufficient to achieve a neutralization of about 6% of said carboxyl groups.

* * * * *